United States Patent [19]

Scheldrup et al.

[11] Patent Number: 5,669,905
[45] Date of Patent: Sep. 23, 1997

[54] ENDOVASCULAR EMBOLIC DEVICE DETACHMENT DETECTION METHOD AND APPARATUS

[75] Inventors: Ronald W. Scheldrup, Menlo Park; Laurent B. Schaller, Los Altos, both of Calif.

[73] Assignee: Target Therapeutics, Inc., Fremont, Calif.

[21] Appl. No.: 481,453

[22] PCT Filed: Mar. 2, 1995

[86] PCT No.: PCT/US95/02635

§ 371 Date: Jul. 11, 1995

§ 102(e) Date: Jul. 11, 1995

[87] PCT Pub. No.: WO95/23558

PCT Pub. Date: Sep. 8, 1995

Related U.S. Application Data

[63] Continuation of Ser. No. 205,512, Mar. 3, 1994, abandoned.
[51] Int. Cl.$^6$ ............................................. A61B 17/38
[52] U.S. Cl. ............................ 606/32; 128/630; 606/41; 606/191
[58] Field of Search ............................. 604/286; 606/32, 606/191, 200, 41; 128/630

[56] References Cited

U.S. PATENT DOCUMENTS

| | | |
|---|---|---|
| 4,057,063 | 11/1977 | Gieles et al. . |
| 4,416,276 | 11/1983 | Newton et al. . |
| 4,739,768 | 4/1988 | Engelson . |
| 4,884,579 | 12/1989 | Engelson . |
| 4,994,069 | 2/1991 | Ritchart et al. . |
| 5,122,136 | 6/1992 | Guglielmi et al. . |
| 5,167,658 | 12/1992 | Ensslin . |
| 5,170,802 | 12/1992 | Mehra . |
| 5,190,517 | 3/1993 | Zieve et al. . |
| 5,226,911 | 7/1993 | Chee et al. . |
| 5,250,071 | 10/1993 | Palermo . |
| 5,300,068 | 4/1994 | Rosar et al. . |
| 5,304,194 | 4/1994 | Chee et al. . |
| 5,341,807 | 8/1994 | Nardella . |
| 5,354,295 | 10/1994 | Guglielmi et al. . |
| 5,382,259 | 1/1995 | Phelps et al. . |
| 5,423,810 | 6/1995 | Goble et al. . |
| 5,423,829 | 6/1995 | Pham et al. . |

OTHER PUBLICATIONS

Becker et al., "Long–term occlusion of the porcine cystic duct by means of endoluminal radio–frequency electrocoagulation" *Radiology* (1988) 167:63–68.

Kopecky et al., "Percutaneous transrenal endoureteral radio–frequency electrocautery for occlusion: Case report" *Radiology* (1989) 170:1047–1048.

*Primary Examiner*—Angela D. Sykes
*Assistant Examiner*—Stephen Huane
*Attorney, Agent, or Firm*—Morrison & Foerster LLP

[57] ABSTRACT

This invention is a method for ensuring for endovascular occlusion through the formation of thrombi in arteries, veins, aneurysms, vascular malformations, and arteriovenous fistulas. In particular, it deals with a method to predictably determine the instant of electrolytic detachment of an embolic device which is introduced to and is intended to remain at the desired thrombus formation site. The invention further includes a method for delivering an embolic device and detecting its electrolytic separation. According to the present invention, DC power with AC superposition is delivered to the sacrificial link that couples a delivery member (e.g., a guidewire) to an occlusion device. The impedance (as measured by the amplitude of the superposed AC) is monitored. When a predetermined change in that impedance (or amplitude occurs), which indicates coil detachment, the DC power is interrupted to minimize or avoid further electrolysis.

22 Claims, 11 Drawing Sheets

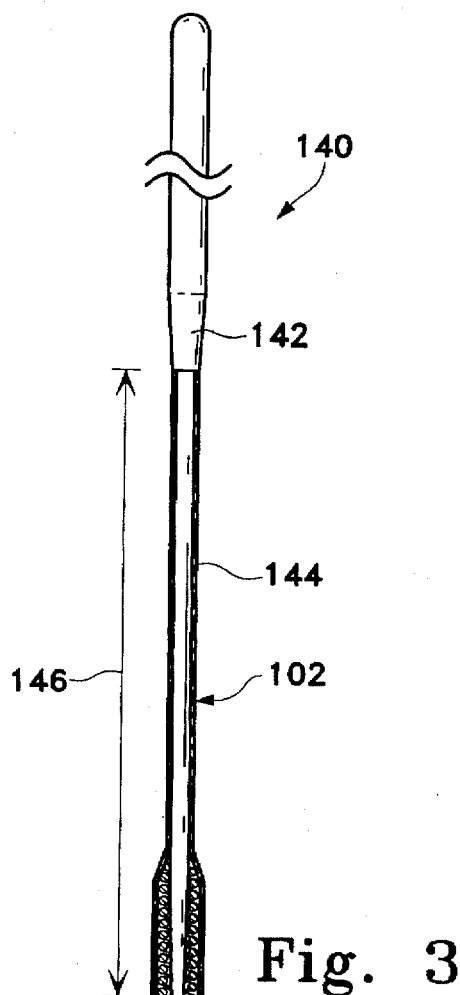
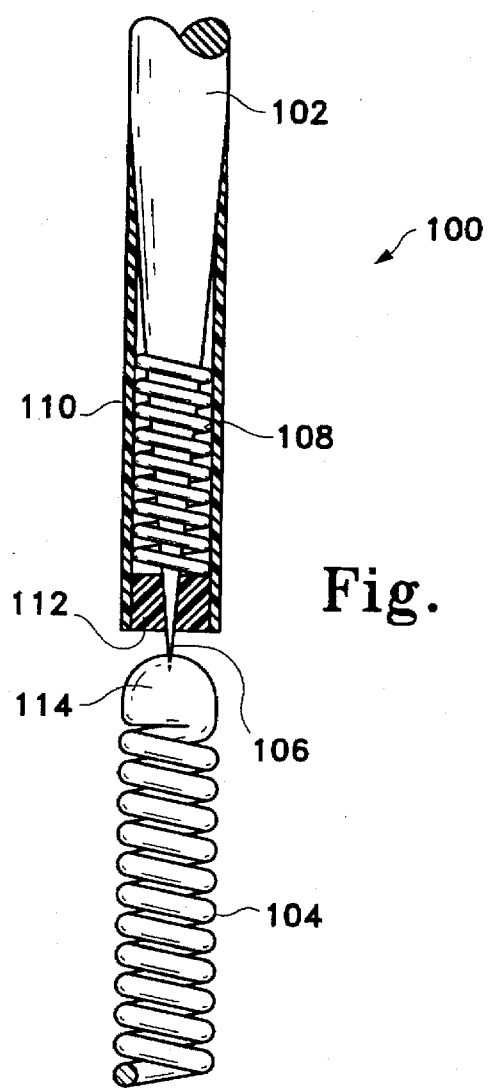
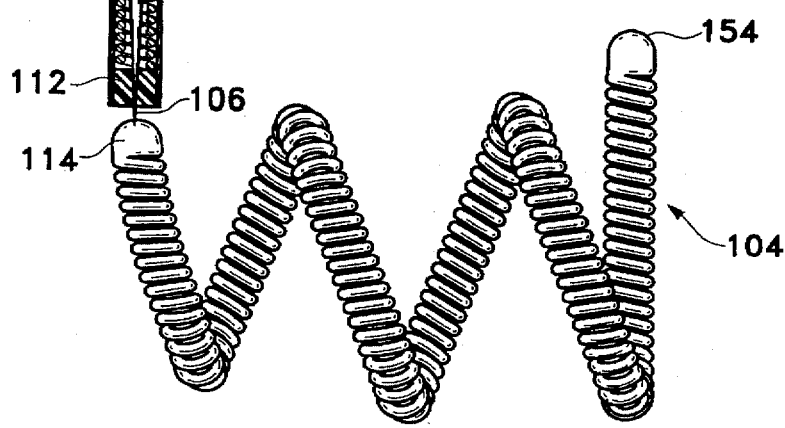
Fig. 2
Fig. 3

ENDOVASCULAR EMBOLIC DEVICE DETACHMENT DETECTION METHOD AND APPARATUS

This is a continuation-in-part of U.S. patent application Ser. No. 08/205,512, filed Mar. 3, 1994, now abandoned, the entirety of which is hereby incorporated herein.

FIELD OF THE INVENTION

The invention generally relates to delivering an occlusion device to a desired site in a mammal to facilitate the formation of mechanical blockage or thrombi in arteries, veins, aneurysms, vascular malformations, and arteriovenous fistulas. More specifically, the invention involves a method and apparatus for detecting electrolytic separation of an endovascular occlusion device from a delivery member after the device has been delivered to the desired site and the coupling between the device and delivery member subjected to an electrolytic environment.

BACKGROUND OF THE INVENTION

Approximately 25,000 intracranial aneurysms rupture each year in North America. The primary purpose of treatment for a ruptured intracranial aneurysm is to prevent rebleeding. There are a variety of ways to treat ruptured and non-ruptured aneurysms.

Possibly the most widely known of these procedures is an extravascular approach using surgery or microsurgery. This treatment is common with intracranial berry aneurysms. The method comprises a step of clipping the neck of the aneurysm, performing a suture ligation of the neck, or wrapping the entire aneurysm. Each of these procedures is formed by intrusive invasion into the body and performed from the outside of the aneurysm or target site. General anesthesia, craniotomy, brain retraction, and placement of a clip around the neck of the aneurysm are typically required in these surgical procedures. The surgical procedure is often delayed while waiting for the patient to stabilize medically. For this reason, many patients die from the underlying disease or defect prior to the initiation of the procedure.

Another procedure—the extra-intravascular approach—involves surgically exposing or stereotactically reaching an aneurysm with a probe. The wall of the aneurysm is then perforated from the outside and various techniques are used to occlude the interior in order to prevent it from rebleeding. The techniques used to occlude the aneurysm include electrothrombosis, adhesive embolization, hog hair embolization, and ferromagnetic thrombosis. These procedures are discussed in U.S. Pat. No. 5,122,136 to Guglielmi et al., the entirety of which is incorporated herein by reference.

A still further approach, the least invasive, is described in Guglielmi et al. It is the endovascular approach. In this approach, the interior of the aneurysm is entered by use of a catheter such as those shown in Engelson (Catheter Guidewire), U.S. Pat. No. 4,884,579 and also in Engelson (Catheter for Guidewire Tracking), U.S. Pat. No. 4,739,768. These patents describe devices utilizing guidewires and catheters which allow access to an aneurysm from remote portions of the body. Specifically, by the use of catheters having very flexible distal regions and guidewires which are steerable to the region of the aneurysm, embolic devices which may be delivered through the catheter are an alternative to the extravascular and extra-intravascular approaches.

The endovascular approach typically includes two major steps. The first step involves the introduction of the catheter to the aneurysm site using devices such as shown in the Engelson patents. The second step often involves filling the aneurysm in some fashion or another. For instance, a balloon may be introduced into the aneurysm from the distal portion of the catheter where it is inflated, detached, and left to occlude the aneurysm. In this way, the parent artery is preserved. Balloons are becoming less in favor because of difficulty in introducing the balloon into the aneurysm sac, the possibility of an aneurysm rupture due to overinflation of the balloon within the aneurysm or due to stress placed on the nonspherically shaped aneurysm by the spherical balloon, and the risk associated with traction produced when detaching the balloon.

A highly desirable embolism-forming device that may be introduced into an aneurysm using endovascular placement procedures, is found in U.S. Pat. No. 4,994,069, to Ritchart et al. The device—typically a platinum/tungsten alloy coil having a very small diameter—may be introduced into an aneurysm through a catheter such as chose described in Engelson above. These coils are often made of wire having a diameter of 2–6 mils. The coil diameter may be 10–30 mils. These soft, flexible coils may be of any length desirable and appropriate for the site to be occluded. For instance, the coils may be used to fill a berry aneurysm. Within a short period of time after the filling of the aneurysm with the embolic device, a thrombus forms in the aneurysm and is shortly thereafter complemented with a collagenous material which significantly lessens the potential for aneurysm rupture.

Coils such as seen in Ritchart et al. may be delivered to the vasculature site in a variety of ways including, e.g., mechanically detaching them from the delivery device as is shown in U.S. Pat. No. 5,250,071, to Palermo or by electrolytic detachment as is shown in Guglielmi et al. (U.S. Pat. No. 5,122,136), discussed above.

Guglielmi et al. shows an embolism-forming device and procedure for using that device. Specifically, the Guglielmi device fills a vascular cavity (such as an aneurysm) with an embolic device, typically a platinum coil, that has been endovascularly delivered. The coil is then severed from its insertion tool by the application of a small electric current. Desirably, the insertion device involves a guidewire which is attached at its distal end to the embolic device by a sacrificial joint that is electrolytically dissolvable. Guglielmi et al. suggests that when the embolic device is a platinum coil, the platinum coil may be 1–50 cm. or longer as is necessary. Proximal of the embolic coil is a guidewire, often stainless steel in construction. The guidewire is used to push the platinum embolic coil, obviously with great gentleness, into the vascular site to be occluded. The patent shows a variety of ways of linking the embolic coil to the pusher guidewire. For instance, the guidewire is tapered at its distal end and the distal tip of the guidewire is soldered into the proximal end of the embolic coil. Additionally, a stainless steel coil is wrapped coaxially about the distal tapered portion of the guidewire to provide column strength to the guidewire. This coaxial stainless steel wire is joined both to the guidewire and to the embolic coil. Insulation may be used to cover a portion of the strength-providing stainless steel coil. This arrangement provides for two regions which must be electrolytically severed before the embolic coil is severed from the guidewire.

U.S. Pat. No. 5,423,829 Nov. 3, 1993, describes a variation of the Guglielmi detachable coil using an improved sacrificial link between the guidewire and the coil. The size of the sacrificial link is limited to allow more precise placement of the embolic device and facile, quick detachment. The focussed electrolysis found at the sacrificial site reduces the overall possibility of occurrence of multiple electrolysis sites and liberation of large particles from those sites.

Previous attempts to detect coil detachment generally involved a DC constant current circuit with a DC voltage monitor (the DC current electrolytically dissolves the sacrificial link). The circuit generally included a DC constant current power source having its positive terminal coupled to the sacrificial link via a guidewire, for example. As discussed above, the link coupled the occlusion device to the guidewire. The negative terminal of the power source typically was coupled to the patient's skin via a large skin electrode (e.g., a ground pad or needle). Other grounding arrangements include providing, an embolic device delivery microcatheter with a cathode that is electrically coupled to the negative terminal of the power source (see U.S. Pat. No. 5,354,295 to Guglielmi et al.). However, the actual moment of detachment of the occlusion device using these schemes may go undetected because detachment of the coil can occur without a corresponding significant increase in DC impedance.

Applicants believe that the electrolytic phenomenon creates the lowest impedance path between the link and ground. This is consistent with certain properties of the coil and sacrificial link, which typically are platinum and stainless steel, respectively. Although the conductivity of stainless steel and platinum are fairly similar under non-reactive environmental conditions, applicants have found that the difference in conductivity between these two materials significantly increases in an electrolytic environment. That is, it takes significantly more voltage for platinum to conduct in the electrolytic solution as compared to stainless steel. More specifically, most of the DC current flows only through the link to the negative electrode. The embolic coil is effectively out of the circuit. As a result, detachment of the coil may go undetected unless the detachment point is at the most proximal point on the sacrificial link.

Applicants have found that the detachment point (i.e., where etching through the link occurs) often is distal from the most proximal point on the link. It is believed that when the electrolysis causes a break in the link downstream from this point, the current still flows through the remaining upstream (proximal) portion of the link and through the body to ground. Since the current continues to flow from the etch site on the linking member, there is no sudden increase in DC impedance at the time of such separation. However, such increase in DC impedance may be detected when all of the upstream (proximal) portion of the sacrificial link finally disintegrates some time considerably later.

In sum, a DC constant current scheme that monitors DC voltage feedback may not detect the precise moment of detachment if the detachment does not occur exactly at the most proximal point on the sacrificial link. Thus, these schemes do not provide the desired repeatability or accuracy in detecting detachment. When detachment goes undetected, one is unable to precisely determine when the system's power should be shut down. The time required for the procedure may be unintentionally increased. In addition, particles may be liberated into the blood stream after coil detachment has occurred.

Thus, there is a need for a system that can accurately detect electrolytic separation of an occlusion device and interrupt the power input in response to detachment detection to discontinue further electrolysis.

SUMMARY OF THE INVENTION

The present invention involves a method and system for detecting electrolytic separation of an occlusion device. The system constructed according to the principles of the present invention comprises a mammalian implant, a delivery member for delivering the implant to a selected site and a link coupling the delivery member to the implant. The system further includes a power supply for supplying DC power with AC superposition to the link. More specifically, the system includes a conductive path and the power supply and link are in that path. The system further includes an AC impedance monitoring circuit also coupled to the path. With this construction, the AC current flows through both the sacrificial link and occlusion device during electrolysis. Accordingly, any sudden or significant change in the monitored AC impedance provides an accurate indication that an open has formed somewhere along the link and the occlusion device has become detached from the delivery member. Thus, unlike a DC voltage monitor, the AC voltage monitor detects separation anywhere along the length of the linking member.

According to another aspect of the invention, the DC power supply to the sacrificial link is interrupted when a sudden change in the monitored AC impedance occurs. In this manner, post detachment electrolysis of the linking member is minimized or avoided.

According to a particular embodiment of the invention, the impedance (as measured by the amplitude of the AC signal) is averaged over time. When a change from the averaged value in excess of 20% is detected, the power input to the sacrificial link is shut off. Changes below this value may be caused by factors other than dissolution of the linking member, which would result in a false indication of detachment. On the other hand, a system that requires more than 40% change may not detect all detachments.

The method for detecting electrolytic separation of an occlusion device according to the present invention includes the steps of (a) providing a delivery member (e.g., a guidewide) and an occlusion device coupled to the delivery member via a link; (b) delivering the occlusion device to a desired site in a mammal via the delivery member; (c) supplying DC power with a superimposed AC signal to the link; and (d) monitoring the amplitude of the superimposed AC signal.

With this method DC power with superposed AC can be interrupted when a sudden change in the amplitude of the superposed AC signal occurs as discussed above. As discussed above, a change of at least about 20% is preferred before triggering power interruption.

The above is a brief description of some of the features and advantages of the present invention. Other features, advantages and embodiments of the invention will be apparent to those skilled in the art from the following description, accompanying drawings and appended claims.

BRIEF DESCRIPTION OF THE DRAWINGS

FIG. 2 is a side view of an electrolytically susceptible, sacrificial link between a core wire and an occlusion device for use in conjunction with the present invention.

FIG. 3 is a side view of a typical corewire assembly for use with the present invention.

DETAILED DESCRIPTION OF THE INVENTION

Figure 1:
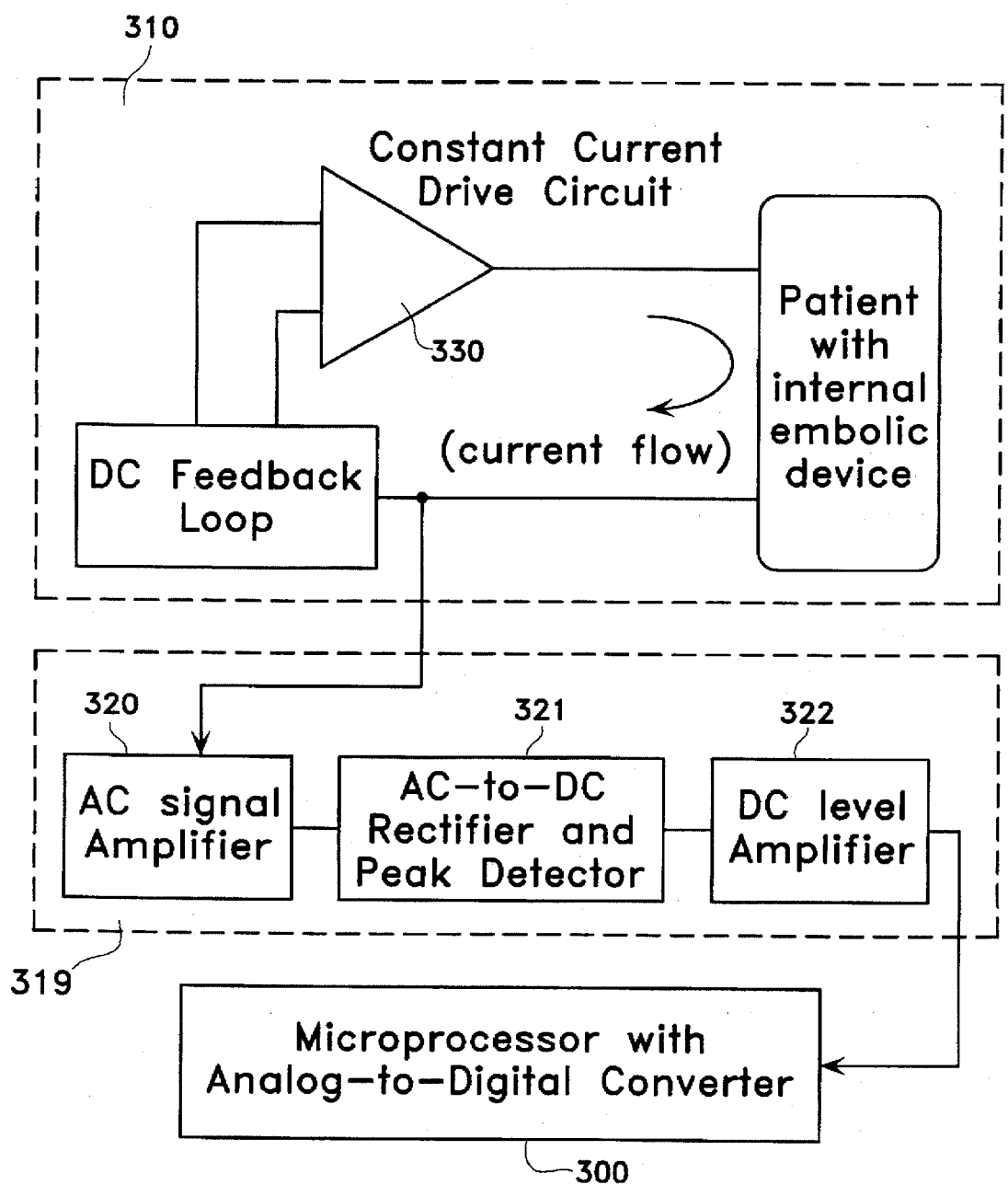
FIG. 1 is a block diagram of a power drive delivery and detection circuit for detecting electrolytic separation of an occlusion device in accordance with the principles of the present invention.

Referring to FIG. 1, a constant current drive circuit and feedback loop 310 and an embolic device detection circuit (EDDC) 319 for detecting the electrolytic separation of an occlusion device from a delivery member or guidewire are shown in accordance with the principles of the present invention. The EDDC includes an AC impedance monitoring circuit and a circuit for detecting changes in the monitored impedance which can comprise microprocessor 300 as will be described in more detail below. The apparatus or system diagrammatically shown in FIG. 1 can be used in conjunction with various occlusion devices such as those described in U.S. Pat. No. 5,122,136 to Guglielmi et al., the entirety of which patent is incorporated herein by reference. A discussion of the electrolytic separation of such devices will be described and followed by description of the preferred power delivery and detection circuits according to the present invention.

Electrolytic separation of a device from a guidewire may be facilitated by means of the assembly 100 shown in FIG. 2. The assembly 100 is made up generally of a guidewire 102 which tapers at its distal end to a point which is soldered into the proximal end of an occlusion device such as vasoocclusive device 104, which in this case is a coil and is of a radiopaque physiologically compatible material such as platinum, tungsten, gold, iridium or alloys of these. All of the guidewire 102 is covered with an insulating material such as Teflon®, polyurethane, polyethylene, polypropylene, or other suitable polymeric material, except the most distal exposed joint or sacrificial link 106. Link 106 is not coated with an electrical insulator and is of a material such as stainless steel, which is susceptible to electrolytic dissolution in blood. Stainless steel guidewire 102 typically is approximately 10–30 mils. in diameter. Often the guidewire is 50–300 cm. in length, that is to say, from the entry site outside the body to sacrificial link 106.

Sacrificial link 106 is a discrete link. By discrete we mean to say preferably that the joint is substantially dissolved upon release of the vasoocclusive device 104. Alternatively, "discrete" may mean that the length of the link 106 is no greater than the diameter of the sacrificial link 106 or that the electrolytic surface present after the vasoocclusive device is released is not substantially greater than would be a circle having the diameter of the sacrificial link 106. Although the latter reduces the likelihood of multiple etch sites, it may still be possible for etching to occur on the remaining exposed section of the link after the vasoocclusive device has been released.

Also shown in FIG. 2 is a coil 108 which is soldered at its proximal end and, typically, is designed to provide some column strength to the guidewire assembly while not detrimentally affecting the flexibility of the tapered portion of the guidewire 102. Obviously, in the area where the support coil 108 is soldered to guidewire 102, the coating on 102 is not present, allowing the solder to adhere to metal surfaces. Further, on the distal tip of core wire 102 may be found a pair of insulators: sleeve 110 and end plug 112 which serve to further remove the stainless steel coil 108 from contact with the blood while the step of electrolytic detachment is carried out. Preferably, the end plug 112 and sleeve 110 are adhesively attached to each other to form an electrically insulating or electrolysis-tight housing about coil 108. The end plug 112 and sleeve 110 form a planar surface which is generally planar and perpendicular to the axis of the core wire 102 (FIG. 2). The shape of the surface is not critical except to the extent it allows reasonably free access of the blood to the sacrificial link 106. Curved, slotted, and other variations of the end surface are also contemplated to be used in this invention.

As noted above, the distal end of the guidewire 102 is inserted into the solder joint 114 forming the proximal end of vasoocclusive device 104. As will be discussed in more detail below, the discrete sacrificial link 106 is completely or substantially completely dissolved during electrolysis.

Vasoocclusive device 104 is shown to be a coil. It may be a coil or a braid or other vasoocclusive device as is already known. The vasoocclusive device may be covered or connected with fibrous materials tied to the outside of the coil or braided onto the outer cover of the coil as desired. Such fibrous adjuvants may be found in U.S. Pat. No. 5,382,259, to Phelps et al, or in U.S. Pat. No. 5,226,911, entitled "Vasoocclusion Coil with Attached Fibrous Elements", the entirety of which are incorporated by reference.

FIG. 3 shows a typical layout involving the sacrificial link 106 as was generally shown in FIG. 2 above. In FIG. 3, a somewhat conventionally Teflon® laminated or similarly insulated stainless steel guidewire 102 may be placed within a protective catheter. As was noted above, stainless steel guidewire 102 may have a diameter of approximately 10–30 mils. In the embodiment illustrated in FIG. 3, a guidewire assembly 140 is shown as including guidewire 102 which is tapered at its distal end to form a conical section 142 which joins a further section 144 which extends along a length of the guidewire designated with reference numeral 146. Section 144 then gradually narrows down to a thinner section 148. The guidewire assembly 140, as noted above, may be placed within a catheter body and is typically 50–200 cm. in length down to sacrificial link 106. As was shown in FIG. 2, the distal section of guidewire assembly 140 has an outer Teflon® sleeve 110 (or sleeve of other appropriate insulating material), which is shown somewhat longer than the sleeve 110 in. FIG. 2. Furthermore, it has an end plug 112 to permit isolation of the guidewire electrically from the blood except at sacrificial discrete link 106. The proximal end of vasoocclusive device 104 is typically a soldered tip or a joint 114. Preferably, vasoocclusive device 104, when a coil, forms a secondary loop after it emanates from the end of the catheter. The distal end of vasoocclusive device 104 may also have an end plug or tip 154 to prevent punctures of the aneurysm when introduced into the aneurysm sac.

Coil or vasoocclusive device 104 may be prebiased to form a cylinder or conical envelope. However, the vasoocclusive device 104 is extremely soft and its overall shape is easily deformed. When inserted within the catheter (not shown), the vasoocclusive device 104 is easily straightened to lie axially within the catheter. Once ejected from the tip of the catheter, vasoocclusive device 104 may form a shape shown in FIG. 3 or may be loosely deformed to conform to the interior shape of the aneurysm.

Figure 4:
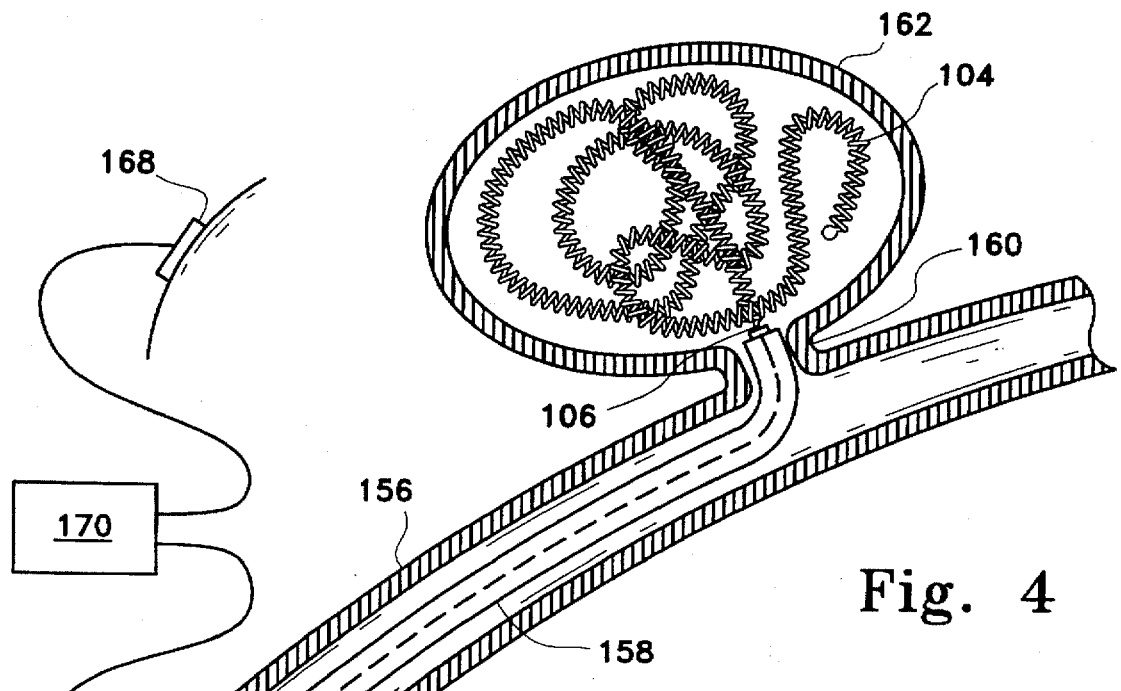
FIGS. 4 and 5 schematically depict the method for deploying an occlusion device according to the present invention.

FIG. 4 shows the placement of an occlusion device described above within an aneurysm. The process of placing an embolic device is typically practiced under fluoroscopic control with local anesthesia. A transfemoral catheter is utilized to treat a cerebral aneurysm and is usually introduced at the groin. The physician guides the distal tip of the catheter to the target site. The embolic device is then inserted into the catheter. Using a fluoroscope, the physician guides the device to the desired position before separation is initiated. When the vasoocclusive device 104 is platinum, it is not effected by electrolysis. When the guidewire and pertinent portions of the supporting coils at the distal tip of the guidewire are adequately coated with insulating coverings, only the exposed portion at the sacrificial link 106 is effected by the electrolysis.

Returning to FIG. 4, catheter 158 is positioned in a vessel 156 with the tip of catheter 158 placed near neck 160 of aneurysm 162. A vasoocclusive device, such as device 104, is fed into aneurysm 162 at least until sacrificial link 106 is exposed beyond the distal tip of the catheter 158. A positive electric current of approximately 0.1–10 milliamps, preferably about 1 milliamp, at 0.1–6 volts, is applied to guidewire 102 (shown in dashed line) to form a thrombus within aneurysm 162 and dissolve sacrificial link 106. Power supply 170 provides DC power with AC superposition as will be discussed in more detail below.

Figure 5:
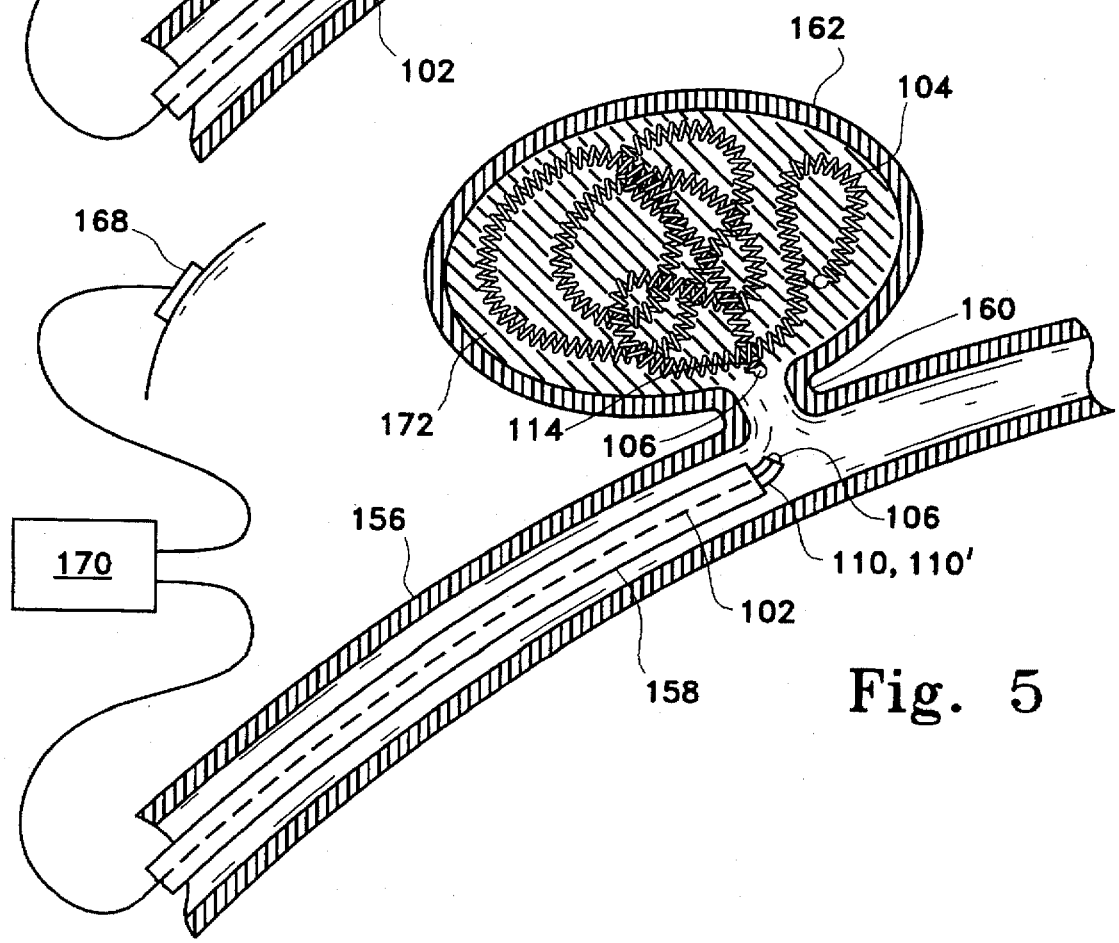

Referring to FIGS. 4 and 5, the positive terminal of power supply 170 is attached to the proximal end of guidewire 102. A negative or return electrode 168 is coupled to the negative terminal of power supply 170. Electrode 168 is typically placed in electrical contact with the skin. Alternatively, the electrode can comprise a ground wire with a skin patch located behind the shoulder of the patient may be used.

After a vasoocclusive device has been properly placed inside the aneurysm 162, the device 104 is detached from guidewire 102 by electrolytic disintegration of sacrificial link 106. After sacrificial link 106 is completely dissolved by electrolytic action, typically within 1–10 minutes, the guidewire 102 is removed from catheter 158 and from vessel 156. Additional vaso-occlusive devices may be placed in aneurysm 162 along with previously detached devices 104 until aneurysm 162 is occluded as shown in FIG. 5. At this point, guidewire 102 and catheter 158 are withdrawn.

Figure 6:
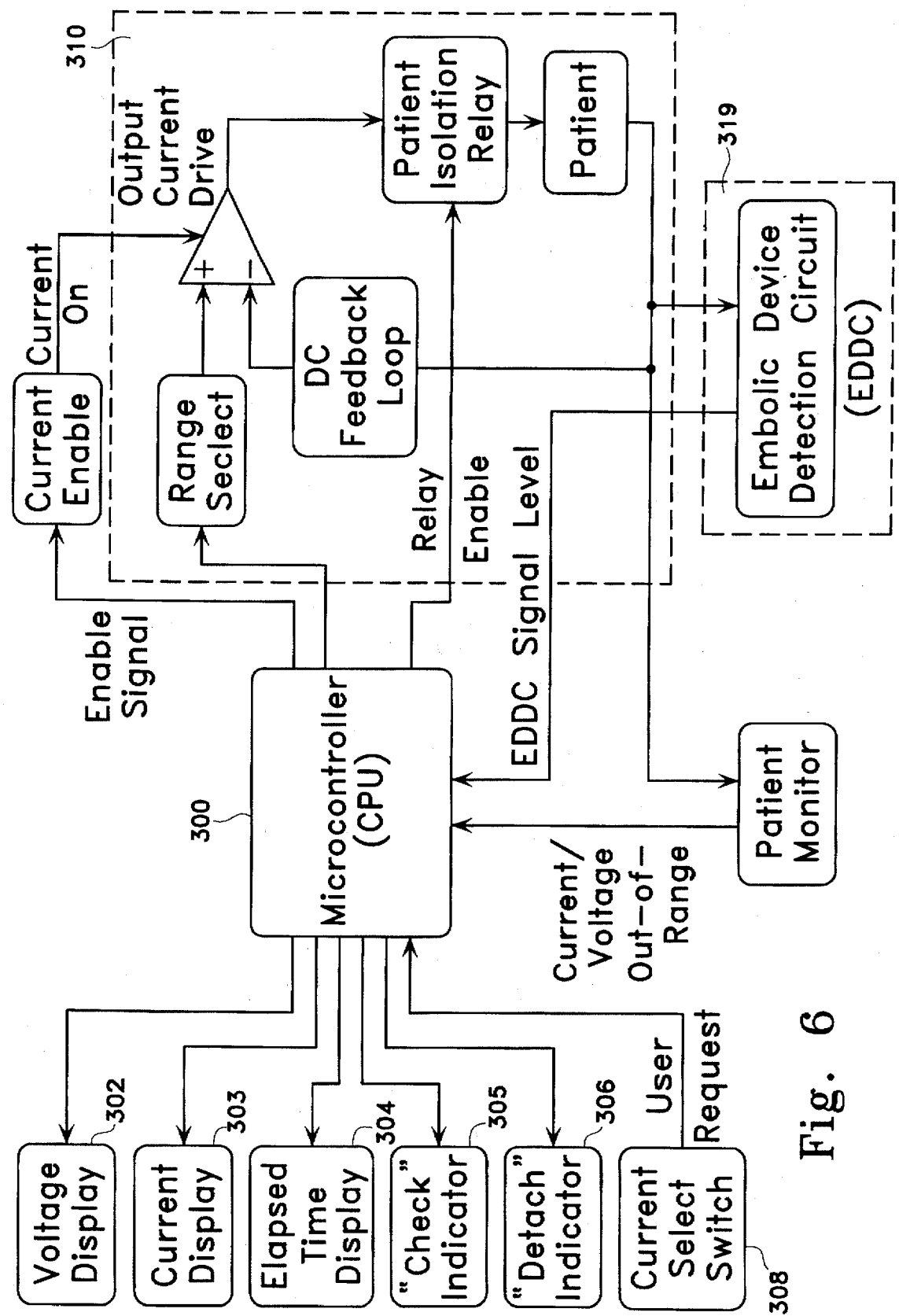
FIG. 6 is a block diagram showing the system of FIG. 1 integrated with a power supply controller according to a preferred embodiment of the invention.

Referring to FIG. 6, a block diagram shows the power drive and detection circuits of FIG. 1 integrated with a power supply controller. A description of the diagram, including description of particular features such as display characteristics follows. However, it should be understood that this description is provided for exemplary purposes and not to limit the invention to particular elements or arrangements discussed below. The voltage display 302, which can be a three digit red LED readout, displays the voltage required to maintain the current flowing through the linking member and the patient. In the preferred embodiment, the fixed-decimal display shows voltages from 0.00 to 9.99 volts DC. In Pause Mode, that is, when electrolytic separation has occurred, and the unit has shut off power to the guidewire, the display shows the voltage immediately prior to coil detachment. The current display 303, which can be a conventional three digit red LED readout, displays the actual current flowing through the linking member and the patient. In the preferred embodiment, the fixed-decimal display shows current from 0.00 to 1.25 mA DC. In addition, the display briefly flashes the new current setting when the current select switch 308 is pressed or when power-up occurs, and then returns to the continuous display of actual current. In Pause Mode, the display shows the current immediately prior to coil detachment. In Normal Mode, the current-select switch 308 is used to change the current setting. When the power supply is turned on, the current is automatically set to 1.00 milliamps. Pressing the current-select switch one time changes the setting to 0.50 milliamps, pressing it a second time changes it to 0.75 milliamps and pressing it a third time returns the setting to 1.00 milliamps. The current may be changed by the physician at any time. Each time the switch is pressed, the current display 303 briefly flashes the new current setting. In Pause Mode, pressing the current-select switch 308 will resume Normal Mode. The current and voltage displays 303 and 302 resume the real-time display of these parameters and the elapsed time display 304 resumes counting from where it was paused.

The elapsed time display 304, which can be a four digit red LED readout, displays the elapsed time in minutes and seconds from the start of the procedure. The flashing colon display shows elapsed time from 00:00 to 59:59. The check indicator 305, which can be a yellow LED indicator, turns on when the microprocessor and EDDC electronics determine that coil detachment has occurred, and indicates that the power supply has entered Pause Mode. The detach indicator 306, which can be a red LED, flashes when the power supply is in Pause Mode after detecting a coil detachment. In each case, the physician is instructed to check detachment using fluoroscopy. In Pause Mode, the display shows the amount of time required to detach the coil.

In the embodiment of FIG. 1, CPU 300, preferably a Motorola MC68HC811E2FN single-chip microcontroller with 2048 bytes of EEPROM, 256 bytes of RAM, an 8 channel 8-bit A/D converter, and three 8-bit I/O ports which control and monitor vital functions of the power supply. However, other processors may be used as would be apparent to one of ordinary skill. In the illustrated embodiment, CPU 300 is shown responsible for monitoring, output DC voltage and current, elapsed time, and requests for changing the DC current. The CPU is outside the critical path of the current control loop, which is implemented in hardware. The CPU manages the LED displays, status indicators and beeper, runs self-diagnostic tests at power-on, issues current setting changes and the fail-safe current enable signal, monitors the EDDC signal to determine when coil detachment has occurred, and monitors the current-select switch.

Referring to FIG. 1, the constant current drive circuit 310 utilizes a feedback loop to maintain the steady current through the patient. The embolic device detection circuit 319, a feedback loop, identifies separation of the embolic device, as reflected in changes in the amplitude of the AC signal from the constant-current source. The AC signal is amplified and rectified by the embolic device detection circuit (EDDC) and is then sent to the CPU for analysis. Although a particular microprocessor has been described, it should be understood that other circuits and topologies (including analog or other nondigital circuits) can be used to monitor and analyze the AC signal to detect changes therein.

In sum, the present invention involves placing an occlusion device, having a sacrificial link coupling the occlusion device to a delivery member (such as a guidewire) at a desired site in a mammal, supplying DC power with AC superposition to the sacrificial link, monitoring the amplitude of the AC signal and detecting any sudden change in that signal. The invention further involves interrupting the DC power input in response to detecting such a sudden change in the AC signal. A preferred embodiment of the embolic device detection circuit (EDDC) is described below with reference to FIG. 7.

Figure 7:
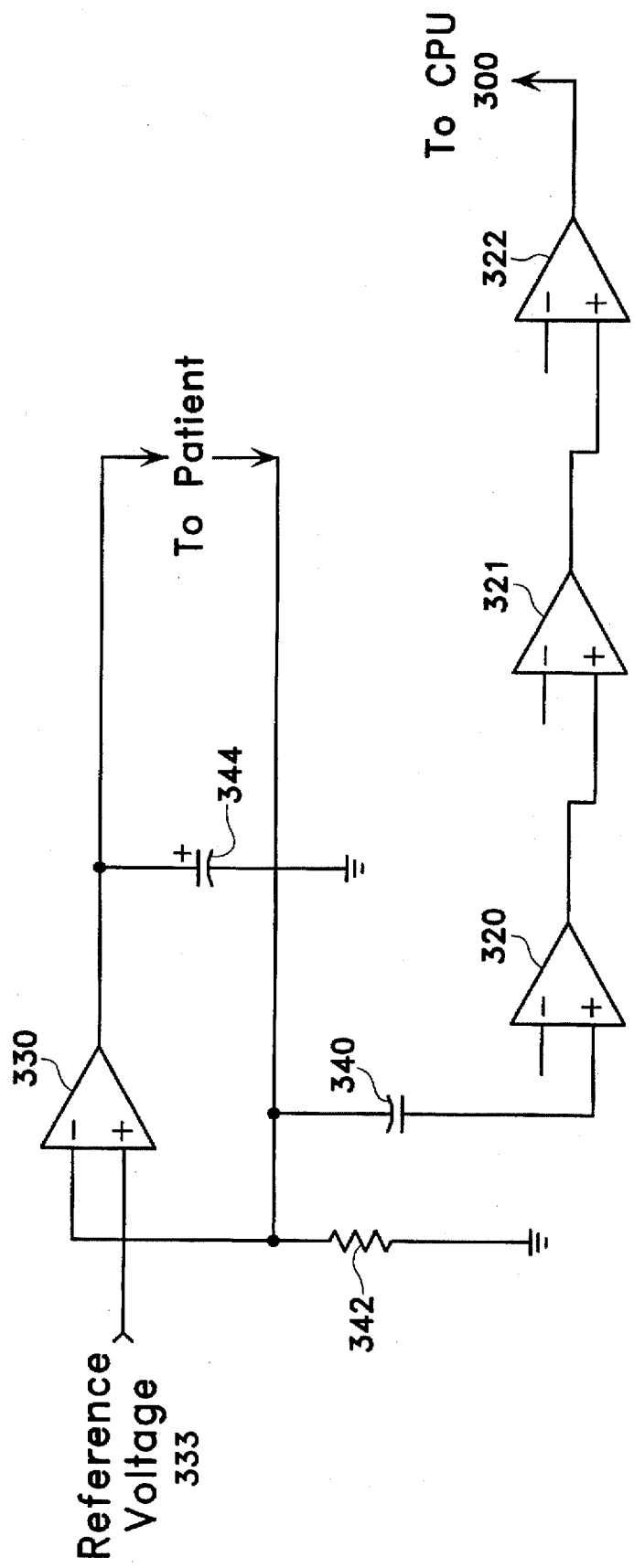
FIG. 7 is a schematic representation of the block diagram of FIG. 1.

The construction of a preferred embodiment of the EDDC is shown in FIG. 7. It is desired to maintain the output of amplifier 330 at a constant current. Amplifier 330 is preferably a National Semiconductor LMC660CN. This device was chosen because of its ability to operate on a single (positive) power supply and because it has a high voltage gain of 126 decibels (dB) and a Gain Bandwidth Product of 1.4 Megahertz (MHz). When the constant current amplifier 330 has achieved equilibrium—when the output current exactly matches the setpoint present at the non-inverting input terminal—the amplifier will oscillate at approximately 20 to 24 kilohertz (kHz) at an amplitude of several hundred millivolts due to a lagging error correction signal (out-of-phase feedback). That is, the amplifier provides constant DC current with AC superposition. The amplitude of this AC signal is dependent on the band-width characteristics of the constant current amplifier and the AC impedance of the steel and the platinum coil and of the patient's body. Capacitor 344, a 4.7 microfarad tantalum capacitor, is used to reduce the amplitude of the self-oscillation voltage to between about 40 to 60 millivolts AC while maintaining a rapid DC response.

Accordingly, a reference voltage 333 is held constant, in this case from 0.166 to 0.332 volts. These voltages represent a constant current output of between 0.5 and 1 milliamp. Resistor 342, with a resistance in this instance of 332 ohms, is connected between the inverting input terminal of amplifier 330 and ground and ensures the maintenance of the constant current flow from amplifier 330.

The constant current flowing out of amplifier 330 flows through the guidewide and to the embolic device. The resistance of the patient's body between the occlusion device and the negative electrode, is generally in the range of 1000 to 4000 ohms and typically about 2000 ohms. Equivalent circuit diagrams of the DC and AC paths are shown in FIGS. 8A and 8B.

Figure 8A:
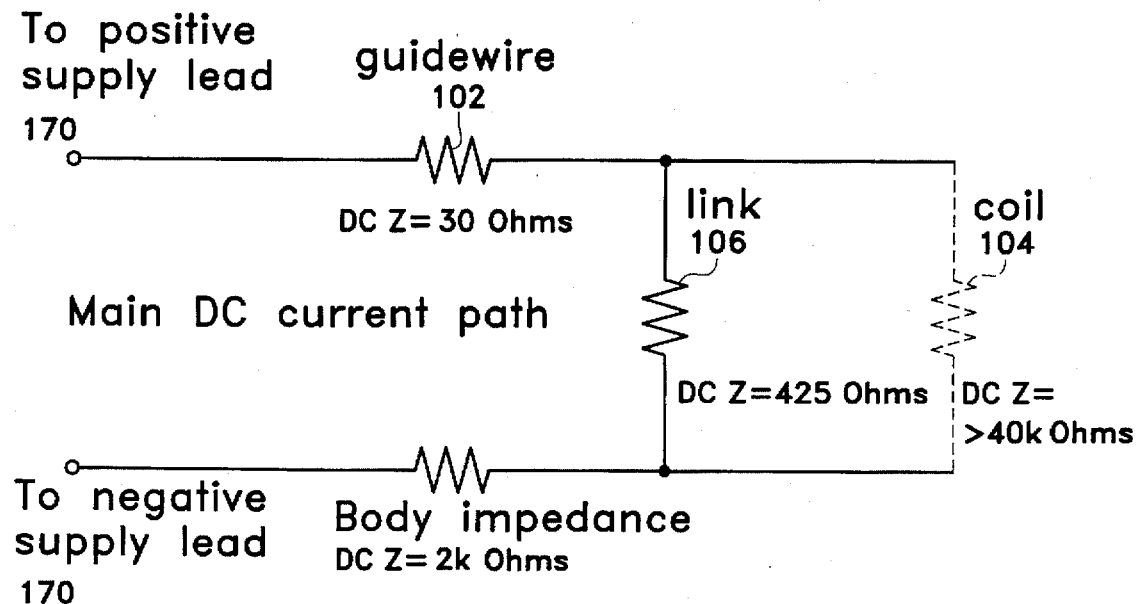
FIGS. 8A and 8F are equivalent circuit diagrams for the DC and AC flow paths within a mammal.

Referring to the illustrative example in FIG. 8A, the impedance (Z) values shown are for a constant voltage input of 2.5V DC or a constant current input of 1.0 mA DC. Although link 106 and embolic device 104 are physically connected in series, immersion in an electrolytic solution provides two parallel DC current paths through the body to ground. The DC current path from link 106 towards ground is caused by ion flow away from the stainless steel link during electrolysis. The current flows in from the left side of guidewire 102 and arrives at the branch of the link 106 and coil 104. More than 99% of the DC current flows through the link 106 with less than 1% flowing through coil 104. Thus, if coil 104 becomes detached and a portion of link 106 remains attached to guidewire 102, the main DC current path remains virtually unchanged.

Figure 8B:
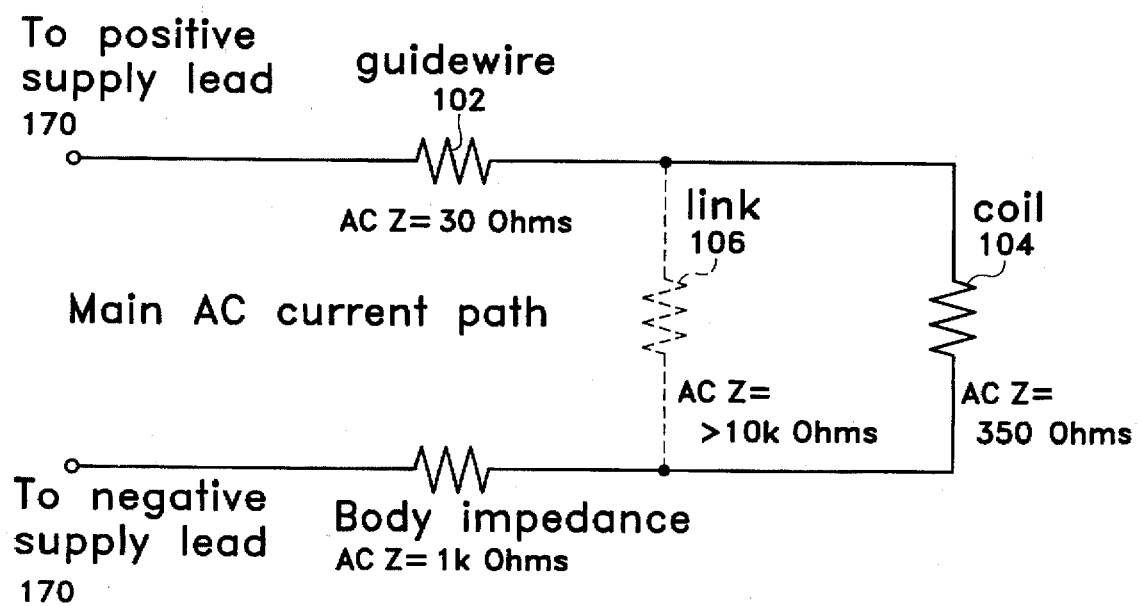

Referring to the illustrative example in FIG. 8B, the impedance (Z) values shown are for a constant voltage input of 2.0V AC at a frequency of 31.25 kHz. As in FIG. 8A, link 106 and coil 104 are physically connected in series. However, immersion in an electrolytic solution does not significantly alter the AC current path so that current flow through the coil can be detected until the coil becomes detached from the guidewire.

In the EDDC (FIG. 7), the AC feedback signal through the patient's body is selectively passed through capacitor 340, in this case, a 0.1 microfarad monolithic capacitor. The AC signal is then amplified in the AC signal amplifier 320, rectified in the AC to DC rectifier 321 and the resulting DC signal is further amplified in DC amplifier 322. The amplified DC signal, the level of which is representative of the amplitude of the error correction voltage of constant current amplifier 330 is then sent to the microprocessor (CPU) 300 for monitoring and analysis as described below. The AC signal, which in illustrated embodiments is a voltage, is monitored by monitoring the level of the amplified DC signal every 10 to 250 milliseconds, preferably every 50 to 200 milliseconds, and constantly averaging the signal every 5 to 50 samples, preferably every 10–20 samples or every 0.5–10 seconds, preferably every 2–6 seconds. In this manner, the CPU can accurately determine the instant the embolic device detaches. When the embolic device detaches, constant current amplifier 330 is no longer in equilibrium and instantly reacts to the change in AC impedance. During the next several dozen milliseconds, amplifier 330 makes large corrections to the DC output voltage to maintain the set current, which disrupts the stable self-oscillation feedback. In other words, the change in AC impedance upsets the balance of the amplifier circuit, and the amplitude of the self-oscillation signal is affected. During this period the amplified EDDC signal will show a sudden voltage drop of greater than 10%, preferably a drop of greater than 20% of the average level for the procedure. This sudden voltage drop reliably detects the dissolution of the junction between the embolic device and the guidewire.

When the sudden voltage drop is detected, the microprocessor immediately halts current flow, energizes the patient isolation relay, freezes the voltage, current and time displays, and emits five beeps to indicate to the physician that coil detachment has occurred. When the power supply is in Pause Mode, no further electrolysis can occur. Using fluoroscopy, the physician can verify that detachment has occurred. If detachment is incomplete and further electrolysis is necessary, the procedure can be resumed by pressing the current-select switch 308 on the front panel. If detachment is verified, the physician can turn off the power supply and withdraw the guidewire. If necessary, another coil can be placed at the site and the power supply started again. If no action is taken, the power supply will automatically turn itself off after 15 minutes.

Figure 9:
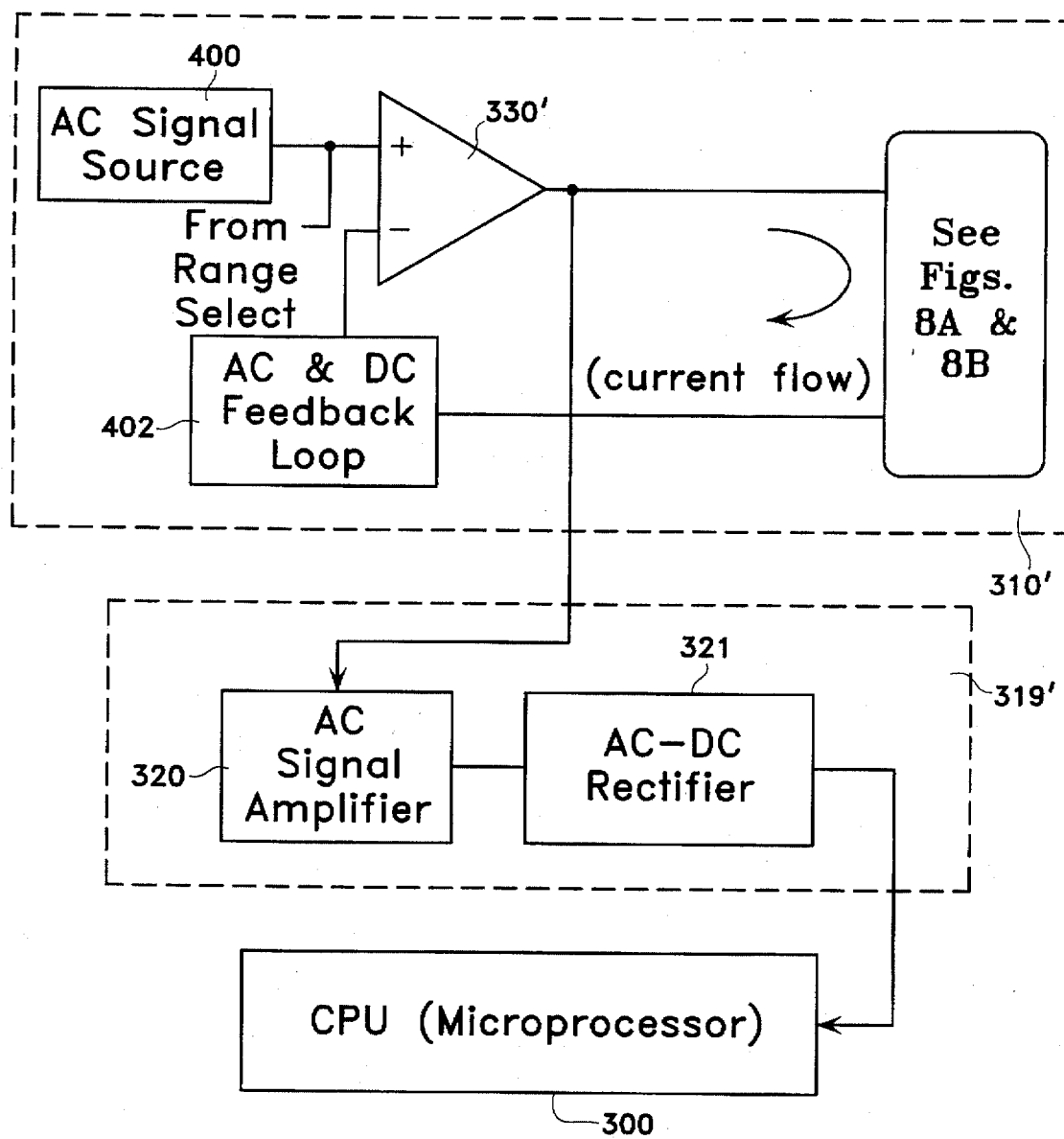
FIG. 9 is a block diagram of an alternative power delivery and detection circuit.
Figure 10:
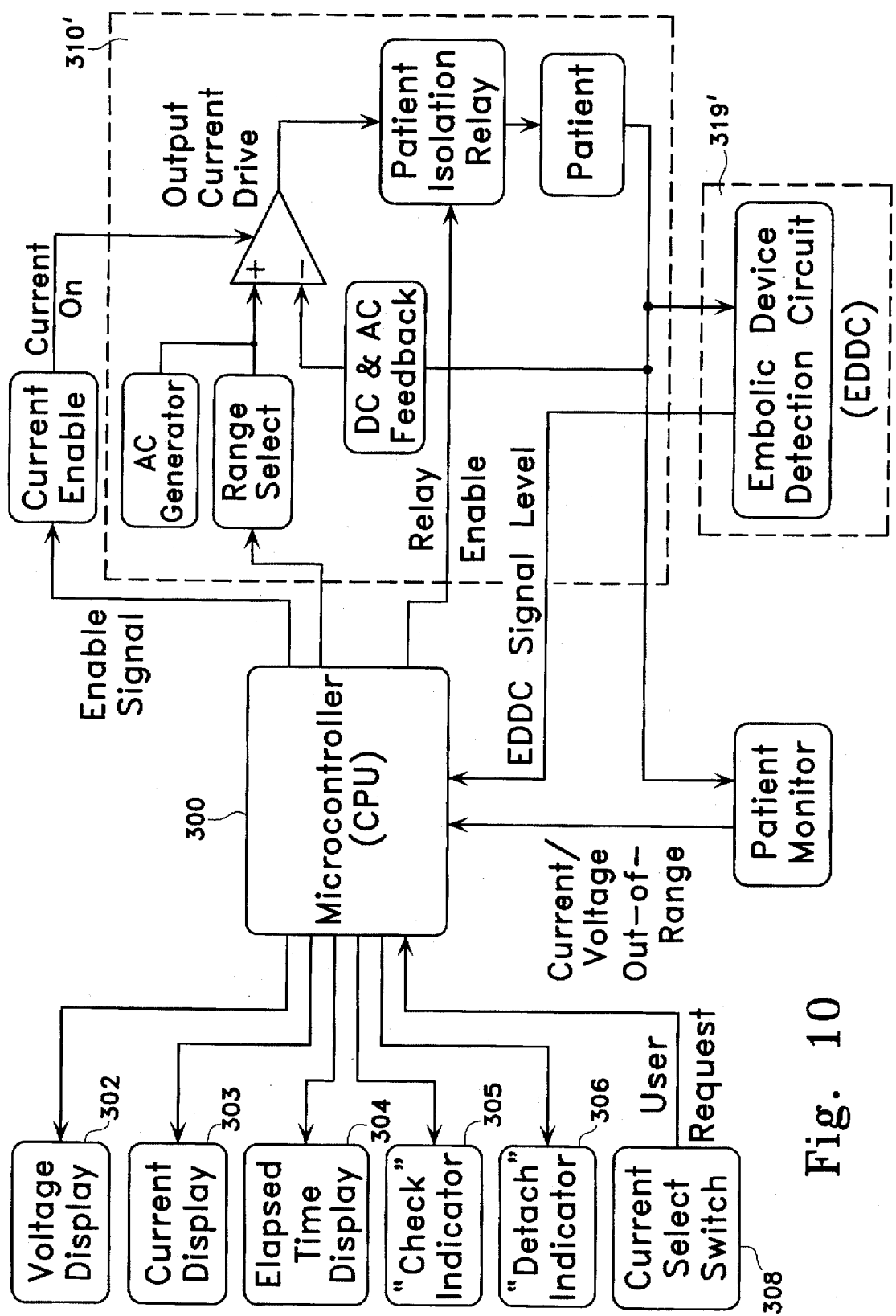
FIG. 10 is a block diagram showing the system of FIG. 9 integrated with a power supply controller as in FIG. 6.
Figure 11:
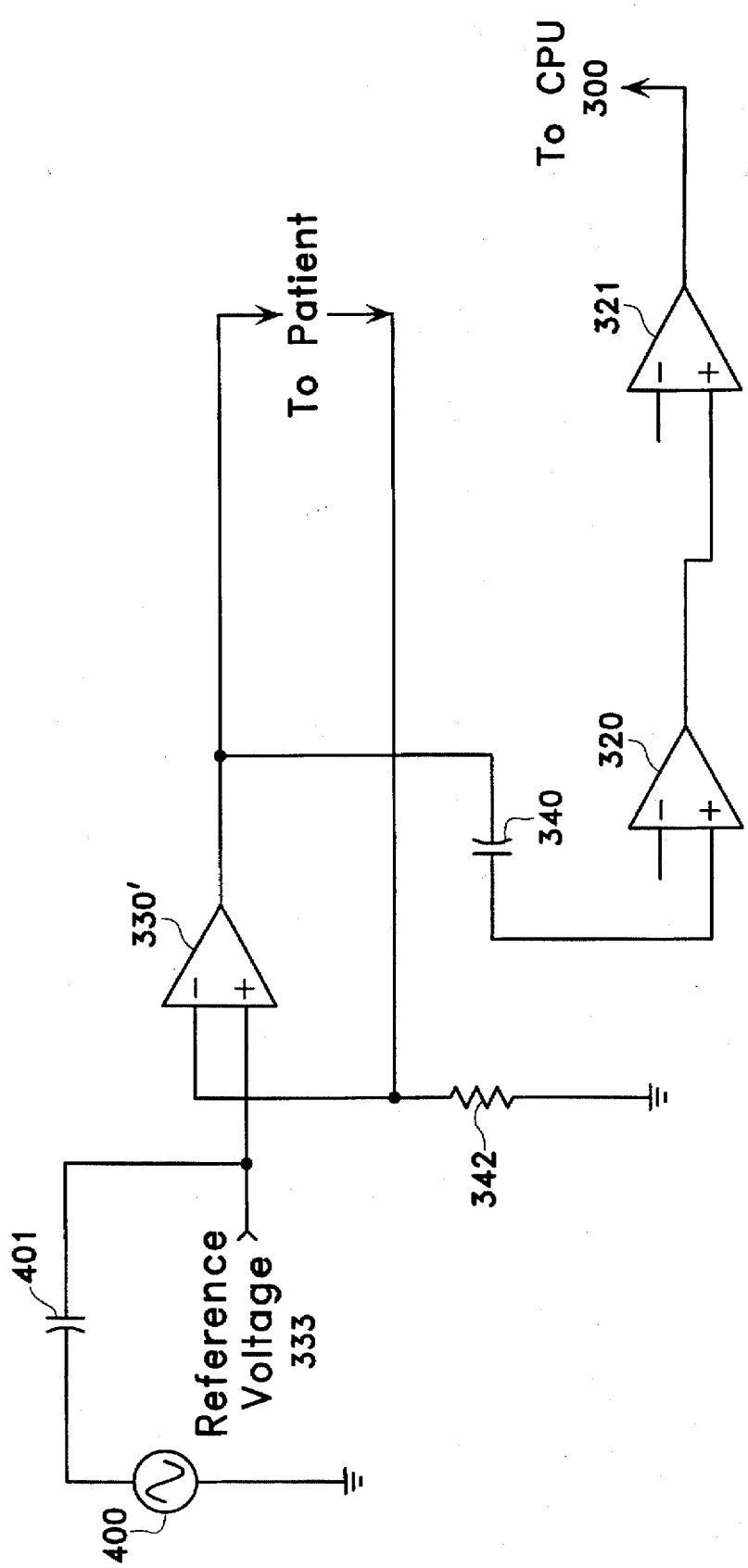
FIG. 11 is a schematic representation of the block diagram of FIG. 9.

Referring to FIGS. 9–11, a further preferred embodiment of the invention is shown. Referring to FIG. 9, the power supply and detection circuit 310' and 319' differ from that shown in FIG. 1 in that an external AC signal source 400 has been added, an AC and DC feedback loop 402 has been substituted for the DC feedback loop (FIG. 1), DC level amplifier 322 has been deleted, and the input to AC signal amplifier 320 comes from the output of the power delivery amplifier (as opposed to from the DC feedback loop of 310). With this arrangement, one can directly monitor the AC impedance by observing the reaction of amplifier 330' in response to the change in AC impedance.

In this embodiment, it is important that the power delivery amplifier remain stable when configured as a constant current source so as not to generate a self-oscillating signal as in the embodiment of FIG. 1. In the embodiment shown in FIG. 1, amplifier 330 oscillated on its own, which allowed the monitoring of the AC impedance by the EDDC. However, there were variations in the self-oscillation signal from unit to unit. This preferred embodiment utilizes an external AC source to ensure all units will show the identical response to changes in AC impedance. Since it is desirable to have the amplifier respond exactly to the AC source, the amplifier must not produce any self-oscillating signal of its own. That is, it must remain stable under constant current conditions. Accordingly, the amplifier shown in FIG. 9 is designated with reference to numeral 330'. One suitable amplifier is a TI2274N amplifier manufactured by Texas Instruments. A constant current source is generally preferred for safety purposes when introducing electricity into a patient.

FIG. 10 shows the additional preferred embodiment of 310' and 319' integrated with the power supply controller as in FIG. 6. The operation of the power supply controller in FIG. 8 is as described for FIG. 6.

Referring to FIG. 11, AC signal source 400 is coupled to the reference input of amplified 330' so as to modulate the output current (i.e., provide AC superposition on the DC current). For purposes of example, a 31.25 kHz 100 mV peak-to-peak sine wave has been found to be a suitable input to the amplifier. Capacitor 401 (FIG. 10) is provided between AC signal source 400 and amplifier 330' to isolate DC bias from the AC signal input. The operation of the constant current source (schematically shown in FIG. 11) is the same as that described with reference to FIG. 7.

In operation, an AC signal is provided to the non-inverting input of amplifier 330' where it is summed with the DC current reference. DC current with AC superposition is output from amplifier 330' and sent to the sacrificial link (e.g., link 106). The DC and AC current paths branch as described above with reference to FIGS. 8A, B. These current paths rejoin at the patient return electrode and continue to AC and DC feedback loop 402. The AC signal is monitored at the output of the constant current amplifier where a measurement of AC impedance can be made through EDDC 319'.

One advantage of the position of this AC signal monitoring point is that the amplitude of the AC signal is higher than in the arrangement of FIG. 1, therefore eliminating the need for additional amplification by amplifier 322.

Referring to FIGS. 9 and 11, the AC signal is monitored at a location upstream from the patient's body. More specifically, the amplitude of the AC signal is monitored through pick-off capacitor 340, in this case, a 0.1 microfarad monolithic capacitor. The AC signal from capacitor 340 is then amplified in the AC signal amplifier 320, and is rectified and peak detected in the AC to DC rectifier 321. The DC signal, the level of which is representative of the amplitude of the AC voltage of constant current amplifier 330 is then sent to the microprocessor (CPU) 300 for monitoring and analysis as described below.

The AC signal, which in the illustrated embodiments is voltage, is monitored by sampling the level of the amplified DC signal every 10 to 250 milliseconds, preferably every 50 to 200 milliseconds, and constantly averaging the signal every 5 to 50 samples, preferably every 10–20 samples or every 0.5–10 seconds, preferably every 2–6 seconds. In this manner, the CPU can accurately determine the instant the occlusion device detaches as discussed below.

When the occlusion device detaches, constant current amplifier 330' instantly reacts to the change in AC impedance. The amplitude of the AC waveform increases in an attempt to maintain the constant AC current set at the non-inverting input. During this period the amplified EDDC signal will show a sudden voltage increase of greater than 20%, preferably an increase of greater than 30% of the average level for the procedure. This sudden voltage increase reliably detects the dissolution of the junction between the embolic device and the guidewire.

When the sudden voltage increase is detected, the microprocessor immediately halts current flow, energizes the patient isolation relay, freezes the voltage, current and time displays, and emits five beeps to indicate to the physician that coil detachment has occurred. When the power supply is in Pause Mode, no further electrolysis can occur. Using fluoroscopy, the physician can verify that detachment has occurred. If detachment is incomplete and further electrolysis is necessary, the procedure can be resumed by pressing the current-select switch on the front panel. If detachment is verified, the physician can turn off the power supply and withdraw the guidewire. If necessary, another coil can be placed at the site and the power supply started again. If no action is taken, the power supply will automatically turn itself off after 15 minutes.

The following Example is intended to illustrate but not to limit the invention in any manner.

EXAMPLE

Figure 12A:
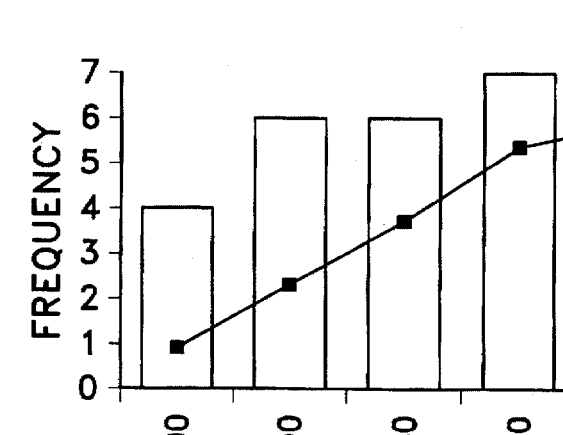
FIGS. 12A and 12B together are table containing a histogram. The information included therein describes release times for the inventive device.
Figure 12B:
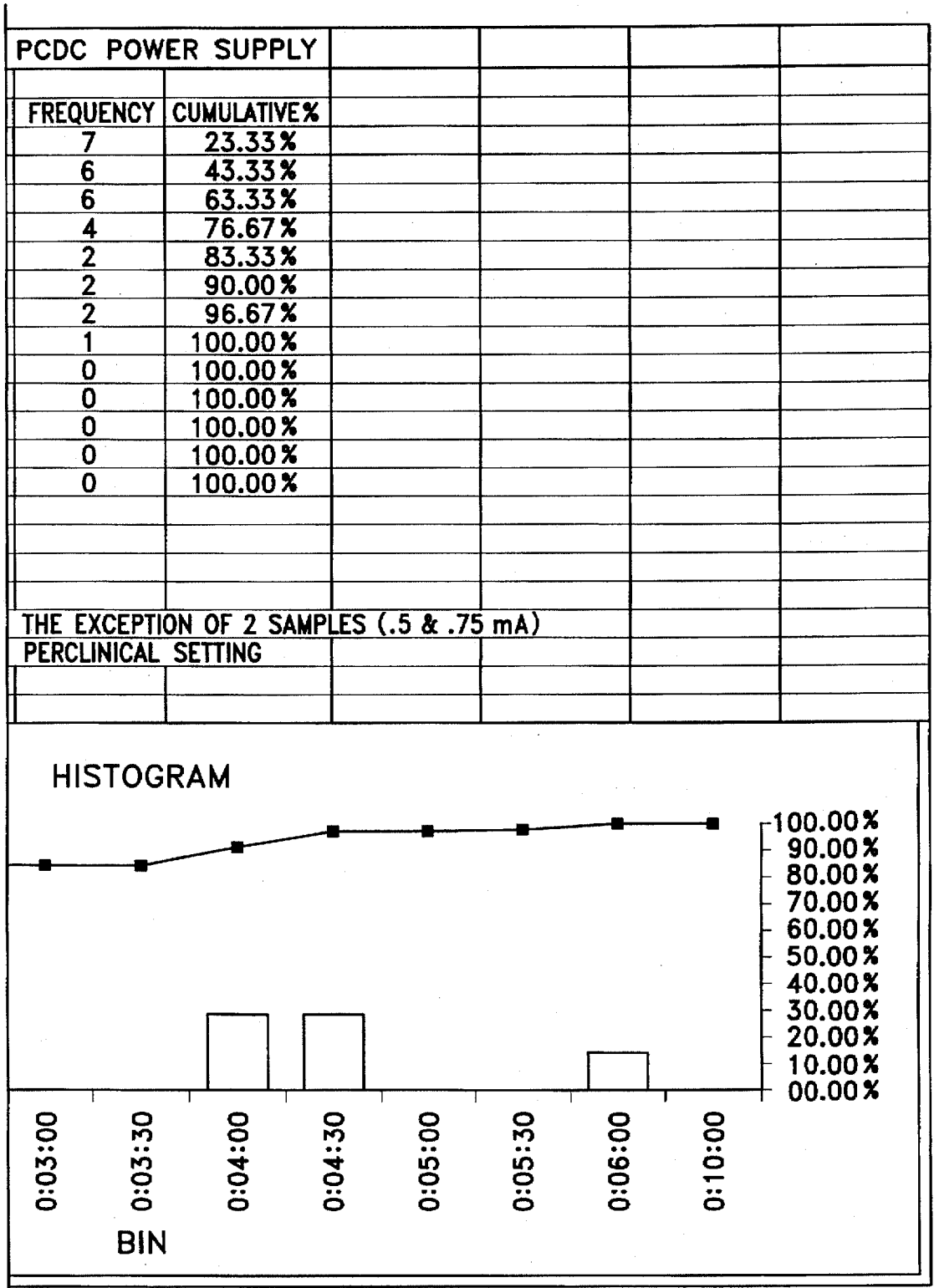

Detachment time studies were run in a preclinical setting using the Guglielmi Detachable Coil (GDC) as described in Guglielmi et al. with the power delivery and detection circuit of FIG. 1 (see FIGS. 12A and 12B). Thirty pigs were anesthetized and catheterized such that a platinum coil was positioned inside the internal carotid artery. The time of coil detachment was determined using the EDDC. For 28 of the samples, at time 0, the 1 milliamp of power was supplied, for one sample 0.5 milliamps of power was supplied and for one sample 0.75 milliamps of power was supplied. The constant current circuit was monitored as was the embolic device detection circuit. As reflected in FIGS. 12A and 12B, detachment occurred in all cases within 6 minutes of supplying power supply and the majority of detachments occurred within 2 minutes.

The above is a detailed description of particular embodiments of the invention. It is recognized that departures from the disclosed embodiment may be made within the scope of the invention and that many alterations and modifications may be made by those having ordinary skill in the art without departing from the spirit and scope of the invention set out in the claims. The full scope of the invention is set out in the claims that follow and their equivalents. For example, although constant current power delivery circuits have been described above with AC voltage monitoring, constant voltage power delivery circuits also can be used and the AC current monitored. The material selection for the guidewire and occlusion device may vary as would be apparent to one of ordinary skill in the art.

We claim as our invention:

1. An implant detachment detection system comprising:
    an implant suitable for implanting in a mammal;
    a delivery member for delivering the implant to a selected site in the mammal;
    a link coupling said delivery member to said implant;
    a power supply circuit for supplying DC power with AC power superposed thereon;
    a conductive path, said power supply circuit and link being in said path; and
    an AC impedance monitoring circuit coupled to said path.

2. The system of claim 1 wherein said monitoring circuit detects changes in the monitored impedance.

3. The system of claim 2 further including an interrupting circuit that interrupts the DC power to the link when a predetermined change in impedance is detected.

4. The system of claim 2 wherein said monitoring circuit generates said signal in response to detection of at least about a 20% change in the AC impedance of said path.

5. The system of claim 2 wherein said monitoring circuit generates a signal indicative of the implant becoming decoupled from said delivery member in response to detecting a predetermined change in impedance.

6. The system of claim 1 further including a circuit for interrupting the DC power supply to the link in response to a sudden change in the monitored impedance.

7. The system of claim 1 wherein said power supply circuit comprises a generator that provides said DC power with superposed AC.

8. The system of claim 1 wherein said power supply circuit comprises a DC power generator and an AC signal generator coupled to said DC generator.

9. The system of claim 1 further including a return electrode in said path, said power supply circuit being located between said link and return electrode in said path and said AC impedance monitoring circuit being coupled to said path between said power supply and link.

10. The system of claim 1 further including a return electrode in said path, said power supply circuit being located between said link and return electrode in said path and said AC impedance monitoring circuit being coupled to said path between said power supply and said return electrode.

11. The system of claim 1 wherein said implant comprises an embolic coil.

12. An implant detachment detection system comprising:

an implant suitable for implantation in a mammal;

a delivery member for delivering the implant to a selected site in the mammal;

a link coupling said delivery member to said implant;

means for providing direct and superposed alternating current to said link; and means for monitoring the alternating current provided by said providing means.

13. The system of claim 12 further including means for interrupting direct current supplied to said link when a predetermined change in the superposed alternating current is detected.

14. An implant detachment system comprising:

an implant adapted for placement in a mammal;

a delivery member for delivering the implant to a selected site in the mammal;

a link for coupling said delivery member to said implant; and a power supply circuit for supplying direct and superposed alternating current to said link concurrently when said implant is at said selected site.

15. The system of claim 14 further comprising a circuit for monitoring alternating current supplied to said link.

16. The system of claim 15 wherein said circuit is adapted for coupling to said mammal when said implant is at said site.

17. The system of claim 14 further comprising a circuit for monitoring alternating current supplied to said link and detecting a change therein.

18. The system of claim 14 further comprising a circuit for isolating alternating current supplied to said link from the direct current supplied to said link so that AC may be monitored.

19. An implant detachment detection system comprising:

an implant adapted for placement in a mammal;

a delivery member for delivering the implant to a selected site in the mammal;

a link detachably coupling said delivery member to said implant; and a power supply circuit for supplying direct and superposed alternating current to said link when said implant is at said selected site.

20. The system of claim 19 further including a circuit for monitoring alternating current supplied to said link.

21. The system of claim 19 wherein said power supply circuit is configured for supplying direct and superposed alternating current to said link.

22. The system of claim 19 further including a circuit for isolating alternating current supplied to said link from direct current supplied to said link.

* * * * *

UNITED STATES PATENT AND TRADEMARK OFFICE

CERTIFICATE OF CORRECTION

PATENT NO. : 5,669,905

DATED : September 23, 1997

INVENTOR(S) : Scheldrup, Robert et al.

It is certified that error appears in the above-identified patent and that said Letters Patent is hereby corrected as shown below:

At column 5, line 56, delete "discrete" and substitute therefor -- "discrete"--.

Signed and Sealed this

Sixteenth Day of December, 1997

Attest:

BRUCE LEHMAN

Attesting Officer

Commissioner of Patents and Trademarks